United States Patent
Pacetti et al.

(10) Patent No.: US 8,895,056 B2
(45) Date of Patent: Nov. 25, 2014

(54) REGIONAL DELIVERY OF THERAPEUTIC AGENTS FOR THE TREATMENT OF VASCULAR DISEASES

(71) Applicant: Abbott Cardiovascular Systems Inc., Santa Clara, CA (US)

(72) Inventors: Stephen D. Pacetti, San Jose, CA (US); Paul M. Consigny, San Jose, CA (US); Ronald W. Heil, Jr., Roseville, MN (US); Florian Niklas Ludwig, Lucerne (CH); Dariush Davalian, San Jose, CA (US); Li Zhao, Mountain View, CA (US); Irina Astafieva, Palo Alto, CA (US); Jinping Wan, Sunnyvale, CA (US); Fozan El-Nounou, Santa Clara, CA (US); Katsuyuki Murase, Cupertino, CA (US); Syed F. A. Hossainy, Hayward, CA (US); Rachel Bright, Claremont, CA (US); Jeffrey Ellis, Atlanta, GA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/725,525

(22) Filed: Dec. 21, 2012

(65) Prior Publication Data

US 2013/0129814 A1 May 23, 2013

Related U.S. Application Data (63) Continuation of application No. 11/639,512, filed on Dec. 15, 2006, now abandoned.

(51) Int. Cl.

| | |
|---|---|
| *A61M 25/10* | (2013.01) |
| *A61K 31/44* | (2006.01) |
| *A61L 29/16* | (2006.01) |
| *A61K 38/17* | (2006.01) |
| *A61K 31/66* | (2006.01) |
| *A61K 31/27* | (2006.01) |
| *A61L 31/16* | (2006.01) |
| *A61K 31/56* | (2006.01) |

(52) U.S. Cl.
CPC .............. *A61M 25/10* (2013.01); *A61K 31/44* (2013.01); *A61L 2300/62* (2013.01); *A61L 29/16* (2013.01); *A61K 38/1709* (2013.01); *A61L 2300/41* (2013.01); *A61L 2300/112* (2013.01); *A61K 31/66* (2013.01); *A61K 31/27* (2013.01); *A61L 31/16* (2013.01); *A61L 2300/416* (2013.01); *A61K 31/56* (2013.01)
USPC .......... 424/450; 424/85.7; 424/400; 514/102; 514/108; 514/107; 514/89; 514/180; 604/509; 604/96.01

(58) Field of Classification Search
None
See application file for complete search history.

(56) References Cited

U.S. PATENT DOCUMENTS

| | | | |
|---|---|---|---|
| 5,258,020 A | 11/1993 | Froix | |
| 5,273,536 A | 12/1993 | Savas | |
| 6,544,223 B1 * | 4/2003 | Kokish | ..................... 604/103.01 |
| 6,632,196 B1 * | 10/2003 | Houser | ....................... 604/96.01 |
| 6,790,372 B2 * | 9/2004 | Roy et al. | ........................ 216/10 |
| 2002/0077592 A1 | 6/2002 | Barry | |
| 2002/0187184 A1 * | 12/2002 | Golomb et al. | ............... 424/450 |
| 2003/0013686 A1 | 1/2003 | Colomb et al. | |
| 2003/0114791 A1 * | 6/2003 | Rosenthal et al. | ......... 604/96.01 |
| 2004/0265391 A1 | 12/2004 | Danenberg et al. | |
| 2004/0266734 A1 | 12/2004 | Danenberg et al. | |
| 2006/0280858 A1 | 12/2006 | Kokish | |
| 2006/0282147 A1 | 12/2006 | Andreas | |

FOREIGN PATENT DOCUMENTS

| | | |
|---|---|---|
| EP | 1 475 054 | 11/2004 |
| FR | 2 797 175 | 2/2001 |
| WO | WO 2004/110303 | 12/2004 |

OTHER PUBLICATIONS

Barasch et al. in Catheterization and Cardiovascular Diagnosis 39:207-212 (1996).*
International Search Report for PCT/US2007/078487, filed Dec. 13, 2007, mailed May 9, 2008, 15 pgs.
Barasch et al., Catheterization and Cardiovascular Diagnosis 39: pp. 207-212 (1996).
Bertoni et al., "Hydroxyapatite/Polyacrylic Acid Nanocrystals", J. Mater. Chem., vol. 9, pp. 779-782 (1999).
Bertoni et al., "Nanocrystals of Magnesium and Fluoride Substituted Hydroxyapatite", Journal of Inorganic Biochemistry, vol. 72, pp. 29-35 (1998).
Boisvert et al., "ApoA1 Reduces Free Cholesterol Accumulation in Atherosclerotic Lesions of ApoE-Deficient Mice Transplanted With ApoE-Expressing Macrophages", Arterioscler. Thromb. Vasc. Biol. vol. 19; pp. 525-5304 (1999).
Bose et al., "Synthesis and Characterization of Hydroxyapatite Nanopowders by Emulsion Technique", Chem. Mater., vol. 15, pp. 4464-4469 (2003).
Chai et al., "Bioactive Nanocrystalline Sol-Gel Hydroxyapatite Coatings", J. of Mat. Science: Materials in Medicine, vol. 10, pp. 465-469 (1999).

(Continued)

*Primary Examiner* — Dennis Heyer
(74) *Attorney, Agent, or Firm* — Squire Patton Boggs (US) LLP (57) ABSTRACT

The present invention relates to the regional delivery of therapeutic agents for the treatment of vascular diseases wherein regional delivery refers to delivery of a therapeutically effective amount of the therapeutic agent to an area of the vessel that includes not only afflicted tissue but non-afflicted tissue at the periphery of the afflicted tissue as well.

24 Claims, 3 Drawing Sheets

(56) References Cited

OTHER PUBLICATIONS

Chow et al., "Propreties of Nanostructured Hydroxyapatite Prepared by a Spray Drying Technique", J. of Res. of the Nat. Inst. of Standards and Techn. vol. 109, No. 6, pp. 543-551 (2004).
Cuneyt Tas, "Synthesis of Biomimetic Ca-Hydroxyapatite powders at 37° C. in synthetic Body Fluids", Biomaterials, vol. 21, pp. 1429-1438 (2000).
Danenberg et al., "Liposomal Alendronate Inhibits Systemic Innate Immunity and Reduces In-Stent Neointimal Hyperplasia in Rabbits", Circulation, vol. 108, pp. 2798-2804 (2003).
Danenberg et al., "Macrophage Depletion by Clodronate-Containing Liposomes Reduces Neointimal Formation After Balloon Injury in Rats and Rabbits", Circulation, vol. 106, pp. 599-605 (2002).
Daniel J. Rader, "High-Density Lipoproteins and Atherosclerosis", The American Journal of Cardiology, vol. 90 (8A) pp. 62-70 (2002).
Danilchenko et al., "Determination of the Bone Mineral Crystallite Size and Lattice Strain from Diffraction Line Broadening", Cryst. Res. Technol., vol. 37, No. 11, pp. 1234-1240 (2002).
David K. Spady, "Reverse Cholesterol Transport and Atherosclerosis Regression", Circulation, vol. 100, pp. 576-578 (1999).
Kim et al., "Polymeric worm micelles as nano-carriers for drug delivery", Nanotechnology, vol. 16, pp. 484-491 (2005).
Layrolle et al., "Sol-Gel Synthesis of Amorphous Calcium Phosphate and Sintering into Microporous Hydroxyapatite Bioceramics", Journal of the American Ceramic Society, vol. 81, No. 6, pp. 1421-1428 (1998).
Li et al., "Differential Effects of Apolipoprotein A-1-Mimetic Peptide on Evolving and Established Atherosclerosis in Apolipoprotein E-Null Mice", Circulation, vol. 110, pp. 1701-1705 (2004).
Yubao et al., "Morphology and Composition of Nanograde Calcium Phosphate Needle-Like Crystals Formed by Simple Hydrothermal treatment", Chapman&Hall, pp. 326-331 (1994).
Libby et al., "Inflammation and Atherosclerosis", Circulation, vol. 105, pp. 1135-1143 (2002).
Lim et al., "Formation of Nanocrystalline Hydroxyapatite in Nonionic Surfactant Emulsions", Langmuir, vol. 15, pp. 7472-7477 (1999).
Lim et al., "Nanosized Hydroxyapatite Powders From Microemulsions and Emulsions Stabilized by a Biodegradable Surfactant", J. Mater. Chem., vol. 9, pp. 1635-1639 (1999).
Lorenceau et al., "Generation of Polymerosomes from Double-Emulsions", Longmuir, vol. 21, pp. 9183-9186 (2005).
Mendez et al., "Synthetic Amphipathic Helical Peptides That Mimic Apolipoprotein A-1 in Clearing Cellular Cholesterol", J. Clin. Invest. The American Society for Clinical Investigation, Inc, vol. 94, pp. 1698-1705 (1994).
Messersmith et al., "Preparation of Calcium-Loaded Liposomes and Their Use in Calcium Phosphate Formation", Chem. Mater., vol. 10, pp. 109-116 (1998).
Mishra et al., "Studies of Synthetic Peptides of Human Apolipoprotein A-I Containing Tandem Amphipathic α-Helixes", Biochemistry, vol. 37, pp. 10313-10324 (1998).
Mönkkönen et al., "Growth Inhibition of Macrophage-like and Other Cell Types by Liposome-encapsulated, Calcium-Bound, and Free Bisphosphonates In Vitro", Journal of Drug Targeting, vol. 11 (5), pp. 279-286 (2003).
Mönkkönen et al., "Growth Inhibition of Macrophage-Like and Other Cell Types by Liposome-encapsulated, Calcium-Bound, and Free bisphosponates In Vitro", Journal of Drug Targeting, vol. 2, pp. 299-308 (1994).
Navab et al., "Human Apolipoprotein A-1 and A-1 Mimetic Peptides: Potential for Atherosclerosis Reversal", Current Opinion in Lipidology, vol. 15, pp. 645-649 (2004).
Nissen et al., "Effect of Recombinant ApoA-1 Milano on Coronary Atherosclerosis in Patients with Acute Coronary Syndromes", Jama, vol. 290, No. 17, pp. 2292-2300 (2003).
Patrick Linsel-Nitschke et al., "HDL As a Target in the Treatment of Atherosclerotic Cardiovascular Disease", Nature Reviews, Drug Discovery, vol. 4, pp. 193-205 (2005).
Pautot et al., "Production of Unilamellar Vesicles Using an Inverted Emulsion", Longmuir, vol. 19, 2870-pp. 2879 (2003).
Qi et al., "Microemulsion-Mediated Synthesis of Calcium Hydroxyapatite Fine Powders", J. of Mat. Science Letters, vol. 16, pp. 1779-1781 (1997).
Rodriguez et al., "Nanocomposites Produced by Growth of Hydroxyapatite Onto Silica Particles Prepared by the Sol-Gel Method", A.C. Letters vol. 5, No. 1 (1996).
Rooijen et al., "Liposome Mediated Depletion of Macrophages: Mechanism of Action, Preparation of Liposomes and Applications", Journal of Immunological Methods, vol. 174, pp. 83-93 (1994).
Takahashi et al., "Multifunctional role of macrophages in the development and progression of atherosclerosis in humans and experimental animals", Med. Electron Microsc., vol. 35, pp. 179-203 (2002).
Utada et al., "Monodisperse Double Emulsions Generated from a Microcapillary Device", Science, vol. 308, pp. 537-541 (2005).
Williams et al., "Rapid Restoration of Normal Endothelial Functions in Genetically Hyperlipidemic Mice by a Synthetic Mediator of Reverse Lipid Transport", Arterioscler. Thromb. Vasc. Biol., vol. 20, pp. 1033-1039 (2000).
Zhang et al., "Preparation and Characterization of Therminally Stable Nanohydroxyapatite", Journal of Mat. Science: Materials in Medicine, vol. 8, pp. 25-28 (1997).

* cited by examiner

REGIONAL DELIVERY OF THERAPEUTIC AGENTS FOR THE TREATMENT OF VASCULAR DISEASES

CROSS-REFERENCE TO RELATED APPLICATION

This application is a continuation of U.S. application Ser. No. 11/639,512, filed on Dec. 15, 2006, which is incorporated by referenced in its entirety, including any drawings, herein.

FIELD

The present invention relates to the regional treatment of vascular diseases.

BACKGROUND

The traditional methods of administering therapeutic agents for the treatment of various diseases have been either systemic or local. Systemic delivery involves the administration of a therapeutic agent at a discrete location followed by the dispersal of the agent throughout the patient's body including, of course, to the target treatment site or organ. In order to achieve a therapeutically effective amount of the agent at the afflicted site, it is usually necessary to administer an initial dose substantially greater than the therapeutically effective amount to account for the dilution the agent undergoes as it travels through the body. Systemic delivery is carried out primarily in two ways: introduction of the therapeutic agent into the digestive tract (enteral administration) or into the vascular system (parenteral administration), either directly such as injection into a vein or an artery or indirectly such as injection into a muscle or into the bone marrow. Delivery by each of these routes is strongly influenced by the so-called ADMET factors: absorption, distribution, metabolism, excretion and toxicity. For enteric administration, such factors as a compound's solubility, its stability in the acidic environs of the stomach and its ability to permeate the intestinal wall all affect the extent to which the drug is absorbed and therefore its bioavailability. For parenteral delivery factors such as enzymatic degradation, the lipophilic/hydrophilic partitioning coefficient, protein binding, etc. will affect the bioavailability of an agent.

Local delivery comprises administration of the therapeutic agent directly to the target site. The ADMET factors tend to be less important than with systemic administration since the agent is being administered essentially directly to the treatment site. Thus, the initial dose can be at or very close to the therapeutically effective amount. With time, some of the locally delivered therapeutic agent may diffuse over a wider region but such is not the intent of localized delivery and the concentration of the diffused agent will ordinarily be sub-therapeutic, i.e., too low to have a therapeutic effect. Since localized delivery targets only the desired treatment site, it is possible that some of the causal factors of the disease that have spread to as yet non-afflicted regions of the organ at the periphery of the afflicted region may not undergo sufficient treatment, resulting in reoccurrence of the disease.

What would be beneficial are devices and methods that can be used to treat a vascular disease such that the ADMET factors are of reduced significance as in the case of local delivery while at the same time some of the broad coverage afforded by systemic delivery is maintained. The current invention provides such devices and methods.

SUMMARY

The present invention provides devices and compositions for and methods of treating vascular disease by the application of therapeutic agents in a "regional" as opposed to "systemic" or "local" manner. In particular, the method comprises providing a device having a regional delivery interface comprising a therapeutic agent, contacting the entire length, or two or more portions of, the delivery interface with a surface of a segment of a vessel that is known or suspected to include a region afflicted with a vascular disease and delivering the therapeutic agent onto or into the surface of the vessel from the portions of the delivery interface in contact with the vessel surface. According to the present invention, the portion or portions of the delivery interface in contact with the surface include not only the known or suspected afflicted region but a portion of the non-afflicted region at the periphery of the afflicted region.

In contrast to systemic and localized delivery, regional delivery, as used herein, refers to the simultaneous delivery of a therapeutically effective amount of a therapeutic agent to a region of the body, which extends beyond the actual afflicted site. That is, the regional delivery of this invention delivers a therapeutic amount of an agent not only to the specific location known or suspected to be afflicted with a vascular disease but also delivers a therapeutic amount to adjoining non-afflicted tissue. In this manner, sub-clinical causal factors related to the disease may be prevented from developing into clinical symptoms after cessation of treatment.

As with local delivery, ADMET is of reduced importance to the regional delivery method of this invention compared to systemic delivery and the initial dose of the therapeutic agent can be closer to the desired therapeutic amount. According to one embodiment of this invention, a therapeutic agent is delivered in therapeutically effective amounts simultaneously and in substantially uniform dose to a segment of a vessel, wherein the segment is at least about 40 mm in length. Another non-limiting example of regional delivery would be to apply a fabric mesh wrap, impregnated with a therapeutic agent, around at least a portion of a vessel or an organ such that the agent is simultaneously delivered in therapeutic amounts over substantially the entire contact surface of the wrap with the vessel or organ.

In an embodiment of the present invention, a device is provided that comprises a regional delivery interface capable of administering a therapeutically effective amount of a therapeutic agent to a segment of a vessel that contains within it a region afflicted with or suspected of being afflicted (hereinafter it is understood that referral to an "afflicted region" refers to both a regions known to be afflicted, a region suspected to be afflicted and/or to a region that is neither known nor suspected to be afflicted but is known or suspected to be particularly susceptible to affliction, i.e., the device and method of this invention may be administered prophylactically) with a vascular disease and a non-afflicted region at the periphery of the afflicted region. Preferably at present, the regional delivery interface is greater than about 40 mm, more particularly between about 40 mm and about 200 mm and more particularly still, between 40 mm and 100 mm in length. The regional delivery interface comprises a therapeutic agent wherein one or more portions of the therapeutic agent-containing delivery interface is/are contacted with a surface of a segment of a vessel that includes both afflicted and non-afflicted regions. The therapeutic agent is then delivered onto or into the surface of the vessel from the portions of the delivery interface in contact with the vessel surface. According to the invention, if two or more portions of the delivery device are contacted with a surface or a segment of a surface of a vessel, the most distant from one another of the two or more portions contact the surface of the vessel at least in part in the non-afflicted region of the vessel at the periphery of the afflicted region.

When the delivery interface comprises a single structure portions of which contact the vessel surface and some of which do not as in the case, without limitation, of a balloon with multiple diameters when inflated such that some portions of the balloon contact the vessel surface and some do not (q.v., below), it is an embodiment of this invention that a therapeutic agent may be delivered from the non-contacting portions of the delivery interface into the space defined by the contacting portions of the delivery interface.

According to an embodiment of the present invention, the therapeutic agent can be administered as a solution in a suitable solvent or as a suspension in a non-solvent carrier using an appropriate delivery interface as described hereinafter. Excipients, i.e., inert materials added to a drug formulation usually to provide stability, bulk and/or a dosage form, can be added if desired.

In another embodiment of the present invention, the therapeutic agent can be formulated as an emulsion, which may be, without limitation, a nanoemulsion.

In a still further embodiment, the therapeutic agent can be incorporated into a carrier such as a micelle, a worm micelle, a liposome, a polymerosome, a microparticle or a nanoparticle comprised of a material other than the therapeutic agent itself. The carrier may be biostable or it may be biodegradable.

Microparticles and nanoparticles can be made of any biocompatible material including, but not limited to a natural, semi-synthetic or synthetic polymers, ceramics or glasses.

As used herein, "biocompatible" refers to a material that in its original intact state and when biologically decomposed into its degradation products is not toxic or at least is minimally toxic to living tissue. A biocompatible material does not, or at least minimally and reparably, injure living tissue. Further, a biocompatible material does not, or at least minimally and controllably, cause an immunological reaction in living tissue.

By "biostable" is meant that the material of which the vehicle is comprised does not appreciably decompose in a physiological environment, for example, without limitation, at physiological pHs or in the presence of enzymes.

Among useful biocompatible, relatively biostable polymers are, without limitation, polyacrylates, polymethacrylates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

Biocompatible, biodegradable polymers include naturally-occurring polymers such as, without limitation, collagen, chitosan, alginate, fibrin, fibrinogen, cellulosics, starches, dextran, dextrin, hyaluronic acid, heparin, glycosaminoglycans, polysaccharides and elastin.

Synthetic biocompatible, biodegradable polymers include, without limitation, polylactic acid, polyglycolic acid, polyethylene glycol, polycaprolactone, polyanhydrides, polyvinyl alcohol and poly(ester-amides).

As used herein, a synthetic polymer refers to one that is created wholly in the laboratory while a semi-synthetic polymer refers to a naturally-occurring polymer than has been chemically modified in the laboratory. Examples of synthetic polymers include, without limitation, polyphosphazines, polyphosphoesters, polyphosphoester urethane, polyhydroxyacids, polyhydroxyalkanoates, polyanhydrides, polyesters, polyorthoesters, polyamino acids, polyoxymethylenes, poly(ester-amides) and polyimides.

Blends or random, alternating, block, random block or graft copolymers of the above polymers may also be used and are within the scope of this invention.

A biostable particle is one that does not appreciably degrade in a physiological environment, i.e., it maintains its particulate shape in the presence of physiological factors such as enzymes and other biologically active substances.

According to another embodiment of the present invention, the therapeutic agent can be in the form of an oil-in-water emulsion, a water-in-oil or a water-in-oil-in-water emulsion.

According to another embodiment of the present invention, the device comprises a balloon and the vessel surface is a luminal surface. The balloon may further comprise a catheter, to the distal end of which the balloon is coupled. In accordance with this embodiment of the invention, the balloon is contacted with the luminal surface by inflation, wherein the inflated balloon comprises substantially one diameter such that the complete outer surface of the balloon is contacted with the luminal surface. Alternatively, the inflated balloon comprises two or more first diameters that define portions of the outer surface of the balloon that are in contact with the luminal surface and one or more second diameters that define portions of the outer surface that are not in contact with the luminal surface, wherein the furthest apart of the two of the portions of the balloon that are in contact with the luminal surface contact the surface in the non-afflicted region of the vessel at the periphery of the afflicted region. At present, it is preferred that the two furthest apart portions are at least about 40 mm, more particularly from about 40 mm to about 200 mm, and more particularly still, from about 40 mm to about 100 mm, apart.

Where the device according to the present invention comprises a balloon, the delivery interface comprises a coating on the outer surface of the balloon, the coating comprising the therapeutic agent.

In the alternative, rather than or in addition to a coating on an outer surface of a balloon, the balloon may be microporous and the therapeutic agent may be contained in a fluid used to inflate the balloon according to methods known in the art.

According other embodiments of the present invention, the delivery interface comprises a plurality of micro-needles disposed at an outer surface of a balloon.

According to another embodiment of the present invention where the surface is a luminal surface, the delivery interface comprises an implantable medical device such as, without limitation, a stent.

According to the present invention, regional treatment of vascular diseases comprises treatment of, without limitation, atherosclerosis, restenosis, vulnerable plaque and peripheral arterial disease using, again without limitation, therapeutic agents that induce apoptosis of macrophages, therapeutic agents that initiate reverse cholesterol transport and anti-inflammatory therapeutic agents.

In an embodiment of this invention, therapeutic agents that induce apoptosis of macrophages include, but are not limited to, bisphosphonates. Bisphosphonates useful with this invention include, but are not limited to, etidronate, clodronate, tiludronate, pamidronate, dimethyl pamidronate, alendronate, ibandronate, risedronate and zeledronate.

In an embodiment of this invention, therapeutic agents that initiate reverse cholesterol transport include, but are not limited to, apolipoprotein A1 and mimetic peptides thereof.

In an embodiment of this invention, therapeutic agents that are anti-inflammatory agent include, but are not limited to, corticosteroids and statins.

DETAILED DESCRIPTION

Brief Description of the Figures

The figures are provided as examples of certain embodiments of this invention to aid in its understanding and are not intended nor are they to be considered as limiting the scope of the invention in any manner whatsoever.

It is to be understood that the use of the singular herein implies the plural and visa versa unless expressly indicated otherwise. For example, without limitation, when the description is directed to the formulation, administration, encapsulation, etc., of a therapeutic agent, the term "therapeutic agent" means a single therapeutic agent or two or more therapeutic agents.

DEFINITIONS

As used herein, "therapeutic agent" refers to any substance that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease. As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded.

As used herein, "treating" refers to the administration of a therapeutically effective amount of a therapeutic agent to a patient known or suspected to be suffering from a vascular disease. A "therapeutically effective amount" refers to that amount of a therapeutic agent that will have a beneficial affect, which may be curative or palliative, on the health and well-being of the patient with regard to the vascular disease with which the patient is known or suspected to be afflicted. A therapeutically effective amount may be administered as a single bolus, as intermittent bolus charges, as short, medium or long term sustained release formulations or as any combination of these. As used herein, short-term sustained release refers to the administration of a therapeutically effective amount of a therapeutic agent over a period from about several hours to about 3 days. Medium-term sustained release refers to administration of a therapeutically effective amount of a therapeutic agent over a period from about 3 day to about 14 days and long-term refers to the delivery of a therapeutically effective amount over any period in excess of about 14 days.

As used herein, a "vascular disease" refers to a disease of the vessels, primarily arteries and veins, which transport blood to and from the heart, brain and peripheral organs such as, without limitation, the arms, legs, kidneys and liver. In particular "vascular disease" refers to the coronary arterial system, the carotid arterial system and the peripheral arterial system. The disease that may be treated is any that is amenable to treatment with a therapeutic agent, either as the sole treatment protocol or as an adjunct to other procedures such as surgical intervention. The disease may be, without limitation, atherosclerosis, vulnerable plaque, restenosis or peripheral arterial disease.

"Atherosclerosis" refers to the depositing of fatty substances, cholesterol, cellular waste products, calcium and fibrin on the inner lining or intima of an artery. Smooth muscle cell proliferation and lipid accumulation accompany the deposition process. In addition, inflammatory substances that tend to migrate to atherosclerotic regions of an artery are thought to exacerbate the condition. The result of the accumulation of substances on the intima is the formation of fibrous (atheromatous) plaques that occlude the lumen of the artery, a process called stenosis. When the stenosis becomes severe enough, the blood supply to the organ supplied by the particular artery is depleted resulting is strokes, if the afflicted artery is a carotid artery, heart attack if the artery is a coronary artery or loss of organ function if the artery is peripheral.

"Restenosis" refers to the re-narrowing or blockage of an artery at or near the where angioplasty or another surgical procedure was previously performed to remove a stenosis. It is generally due to smooth muscle cell proliferation at times accompanied by thrombosis. Prior to the advent of implantable stents to maintain the patency of vessels opened by angioplasty, restenosis occurred in 40-50% of patients within 3 to 6 months of undergoing the procedure. Post-angioplasty restenosis before stents was due primarily to thrombosis or blood-clotting at the site of the procedure. While the use of IIIb-IIIa anti-platelet drugs such as abciximab and epifabatide, which are anti-thrombotic, reduced the occurrence of post-procedure clotting and stents reduced it even further (although stent placement itself can initiate thrombosis), stent placement sites are also susceptible to restenosis due to abnormal tissue growth at the site of implantation. This form of restenosis tends also to occur at 3 to 6 months after stent placement but it is not affected by the use of anti-clotting drugs. Thus, alternative therapies are continuously being sought to mitigate, preferably eliminate, this type of restenosis. Drug eluting stents (DES) which release a variety of therapeutic agents at the site of stent placement have been in use for some time. These stents, however, have to date comprised delivery interfaces that are less than 40 mm in length and in any event have delivery interfaces that are not intended, and most often do not, contact the luminal surface of the vessel in which they are implanted at the non-afflicted region at the periphery of the afflicted region.

"Vulnerable plaque" refers to an atheromatous plaque that has the potential of causing a thrombotic event and is usually characterized by a very thin wall separating it from the lumen of an artery. The thinness of the wall renders the plaque susceptible to rupture. When the plaque ruptures, the inner core of usually lipid-rich plaque is exposed to blood, with the potential of causing a potentially fatal thrombotic event through adhesion and activation of platelets and plasma proteins to components of the exposed plaque.

The phenomenon of "vulnerable plaque" has created new challenges in recent years for the treatment of heart disease. Unlike occlusive plaques that impede blood flow, vulnerable plaque develops within the arterial walls, but it often does so without the characteristic substantial narrowing of the arterial lumen which produces symptoms. As such, conventional methods for detecting heart disease, such as an angiogram, may not detect vulnerable plaque growth into the arterial wall.

The intrinsic histological features that may characterize a vulnerable plaque include increased lipid content, increased macrophage, foam cell and T lymphocyte content, and reduced collagen and smooth muscle cell (SMC) content. This fibroatheroma type of vulnerable plaque is often referred to as "soft," having a large lipid pool of lipoproteins surrounded by a fibrous cap. The fibrous cap contains mostly collagen, whose reduced concentration combined with macrophage-derived enzyme degradations can cause the fibrous cap of these lesions to rupture under unpredictable circumstances. When ruptured, the lipid core contents, thought to include tissue factor, contact the arterial bloodstream, causing a blood clot to form that can completely block the artery resulting in an acute coronary syndrome (ACS) event. This type of atherosclerosis is coined "vulnerable" because of unpredictable tendency of the plaque to rupture. It is thought that hemodynamic and cardiac forces, which yield circumferential stress, shear stress, and flexion stress, may cause disruption of a fibroatheroma type of vulnerable plaque. These forces may rise as the result of simple movements, such as getting out of bed in the morning, in addition to in vivo forces related to blood flow and the beating of the heart. It is thought that plaque vulnerability in fibroatheroma types is determined primarily by factors which include: (1) size and consistency of the lipid core; (2) thickness of the fibrous cap covering the lipid core; and (3) inflammation and repair within the fibrous cap.

Peripheral vascular diseases are generally caused by structural changes in blood vessels caused by such conditions as inflammation and tissue damage. A subset of peripheral vascular disease is peripheral artery disease (PAD). PAD is a condition that is similar to carotid and coronary artery disease in that it is caused by the buildup of fatty deposits on the lining or intima of the artery walls. Just as blockage of the carotid artery restricts blood flow to the brain and blockage of the coronary artery restricts blood flow to the heart, blockage of the peripheral arteries can lead to restricted blood flow to the kidneys, stomach, arms, legs and feet.

As used herein, an "afflicted region" of a vessel is a region that exhibits clinical manifestations of disease, such as macroscopic evidence in the form of, without limitation, obvious luminal wall thickening, inflammation, etc. or microscopic evidence in the form of, again without limitation, an accumulation of monocytes, macrophages, neutrophiles, smooth muscle cells, inflammatory cytokines, various lipoproteins, etc.

As used herein, a "non-afflicted region" of a vessel is a region that does not exhibit a clinical manifestation of the disease and appears as healthy tissue. "Non-afflicted regions at the periphery of the afflicted region" refers to healthy tissue at the border between afflicted and non-afflicted regions.

As used herein, a "device" refers to any manner of apparatus that is used or that may be used to in conjunction with a delivery interface of this invention. The device may be transitory, that is, it may be a device that is inserted into a patient's body for only so long as is necessary to administer a therapeutic agent to the patient from a delivery interface of the device or it may be an implantable medical device intended to remain in a patient's body for longer than necessary to deliver the therapeutic agent, possibly for as long as the remaining lifetime of the patient. Intermediate between transitory devices and implantable medical devices intended to remain in place permanently are biodegradable implantable medical devices which over time degrade to substances that can either be adsorbed into or excreted by the body.

An example, without limitation, of a transitory device is a vascular catheter. A vascular catheter is a thin, flexible tube with a manipulating means at one end, referred to as the proximal end, which remains outside the patient's body, and an operative device at or near the other end, called the distal end, which is inserted into the patient's artery or vein. The catheter is often introduced into a patient's vasculature at a point remote from the target site, e.g., into the femoral artery of the leg where the target is in the vicinity of the heart. The catheter is steered, assisted by a guide wire than extends through a lumen in the flexible tube, to the target site whereupon the guide wire is withdrawn at which time the lumen may be used for the introduction of fluids, often containing therapeutic agents, to the target site.

An "implantable medical device" refers to any type of appliance that is totally or partly introduced, surgically or medically, into a patient's body or by medical intervention into a natural orifice, and which is intended to remain there after the procedure. As used herein, patient refers to either a medical or veterinary patient. As noted above, the duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, self-expandable stents, balloon-expandable stents, stent-grafts, grafts, artificial heart valves and cerebrospinal fluid shunts.

Examples of implantable medical devices are, without limitation, vessel wraps and stents. A vessel wrap is a thin sheet of flexible material, which may be fabric, polymer, metal, etc. that is literally wrapped around the outside of a vessel and is in contact with the outer surface. The wrap may be solid or it may be formed in virtually any manner of desired pattern such as, without limitation, a mesh, a ribbed polymeric structure or an embossed metal sheet.

As used herein, a "stent" refers generally to any device used to hold tissue in place in a patient's body. Particularly useful stents, however, are those used for the maintenance of the patency of a vessel in a patient's body when the vessel is narrowed or closed due to diseases including, without limitation, tumors (in, for example, bile ducts, the esophagus, the trachea/bronchi, etc.), benign pancreatic disease, coronary artery disease, carotid artery disease and peripheral arterial disease such as atherosclerosis, restenosis and vulnerable plaque. A stent can be used in, without limitation, neuro, carotid, coronary, pulmonary, aorta, renal, biliary, iliac, femoral and popliteal arteries as well as other peripheral vasculatures. A stent can be used in the treatment or prevention of diseases such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents, including in particular those of this invention, may be employed for the delivery of therapeutic agents to specific treatment sites in a patient's body. In fact, therapeutic agent delivery may be the sole purpose of the stent or the stent may be primarily intended for another use such as those discussed above with drug delivery providing an ancillary benefit. For the purpose of this invention a stent would be coated with a layer of material comprising one or more therapeutic agents, the layer comprising a delivery interface of this invention that is at least about 40 mm in length.

Figure 1:
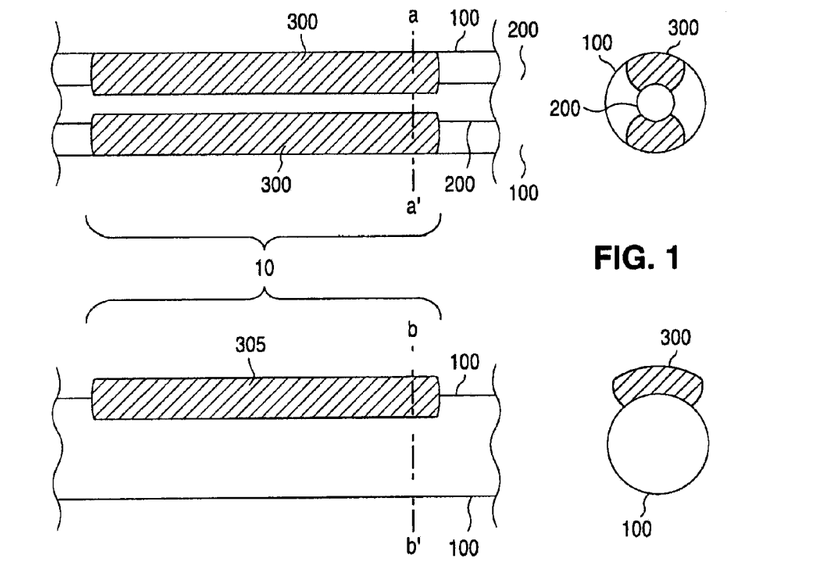
FIG. 1 is a schematic depiction of an embodiment of this invention involving the contact of a circumferentially non-continuous, linearly continuous segment of a vessel with a delivery interface of this invention.
Figure 2:
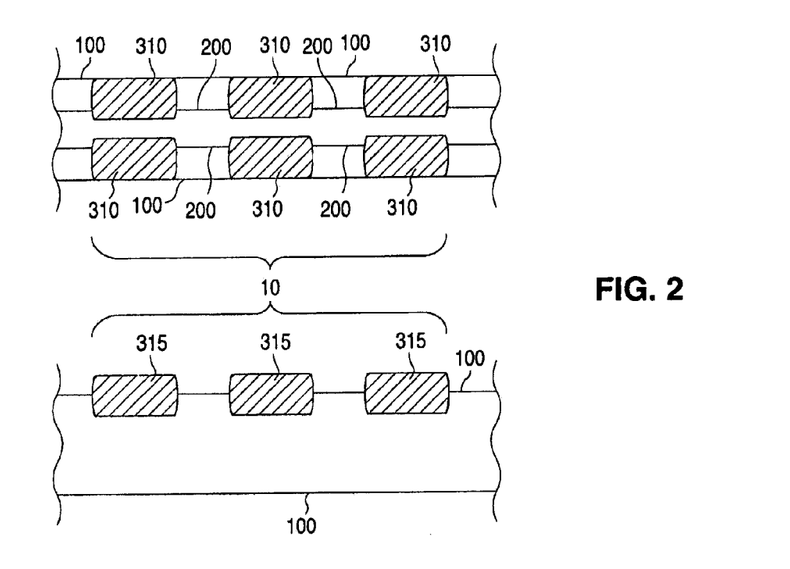
FIG. 2 is a schematic depiction of an embodiment of this invention involving the contact of a circumferentially non-continuous, linearly non-continuous segment of a vessel with a delivery interface of this invention.
Figure 3:
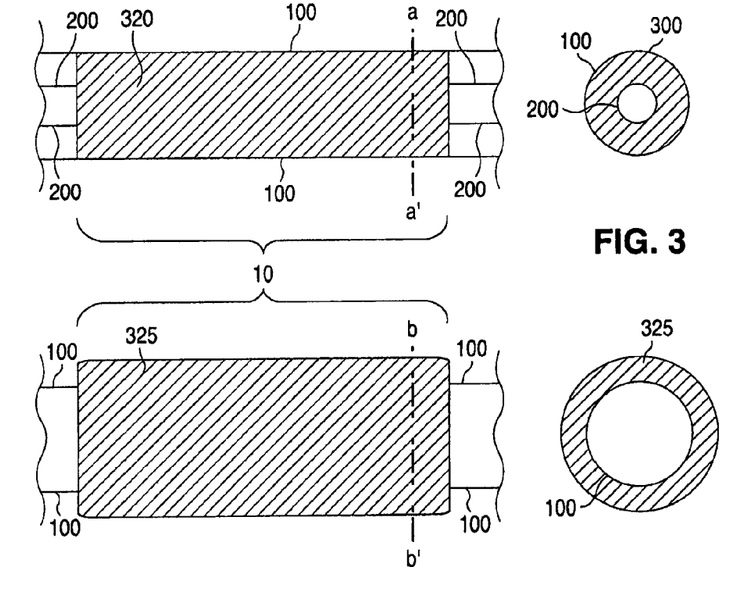
FIG. 3 is a schematic depiction of an embodiment of this invention involving the contact of a circumferentially continuous, linearly continuous segment of a vessel with a delivery interface of this invention.
Figure 4:
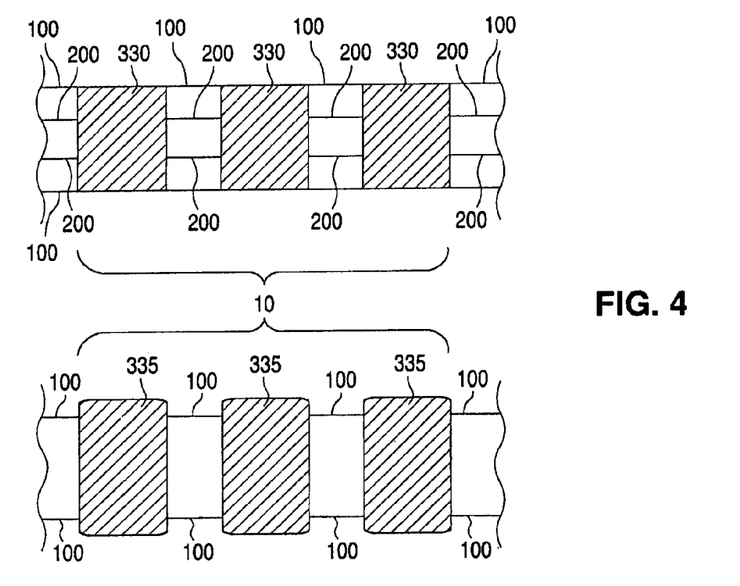
FIG. 4 is a schematic depiction of an embodiment of this invention involving the contact of a circumferentially continuous, linearly non-continuous segment of a vessel with a delivery interface of this invention.

As used herein, a "delivery interface" refers to a surface region of a device of this invention that is capable of providing treatment to an area of the vessel that is greater than that which is accomplished with local delivery interfaces known in the art. That is, the delivery interface of this invention provides treatment to area of a vessel that includes not only the afflicted region of the vessel but non-afflicted regions at the periphery of the afflicted region. Preferably, when device according to the present invention is fully deployed, the delivery interface is capable of being placed in intimate contact with all or portions of a surface of an at least about 40 mm long segment of a blood vessel and is further capable of delivering a therapeutic amount of the therapeutic agent onto or into the surface of the segment wherever it is in intimate contact with the vessel surface, with the proviso that if the device is in contact only with portions of the surface, two of the contact regions are located at least partially in the above-mentioned periphery of the afflicted region. At present it is preferred that such contact regions be at least about 40 mm apart. Since blood vessels are essentially tubular, i.e., circular in cross-section with a central lumen defined by an interior surface (the luminal surface) and an exterior surface (the adventitial surface), a "delivery interface" of this invention will be capable of delivering a therapeutic agent to the surface in a variety of configurations including, without limitation, the following: (a) FIG. 1 schematically depicts a segment of a luminal surface of vessel wall 100 contacted by circumferentially non-continuous, linearly continuous surface 300 of delivery interface 10, which has been directed to the afflicted site by device 200, which may be, without limitation, a catheter, or an adventitial surface of vessel wall 100 contacted by circumferentially non-continuous, linearly continuous surface 305 of delivery interface 10; (b) FIG. 2 schematically depicts a segment of a luminal surface of vessel wall 100 contacted by circumferentially non-continuous, lineally non-continuous surfaces 310 of delivery interface 10 which has been directed to the afflicted site by device 200, which may be, without limitation, a catheter, or an adventitial surface of vessel 100 contacted by circumferentially non-continuous, lineally non-continuous surfaces 315 of delivery interface 10; (c) FIG. 3 schematically depicts a segment of a luminal surface of vessel wall 100 contacted by circumferentially continuous, linearly continuous surface 320 of delivery interface 10, which may be directed to the afflicted site by device 200, which can be, without limitation, a catheter, or an adventitial surface of vessel wall 100 contacted by circumferentially continuous, linearly continuous surface 325 of delivery interface 200; or, (d) FIG. 4 schematically depicts a segment of a luminal surface of vessel 100 contacted by circumferentially continuous, linearly non-continuous surface 330 of delivery interface 10, wherein the delivery interface may be directed to the afflicted site by device 200, which can be, without limitation, a catheter, or an adventitial surface of vessel 100 contacted by circumferentially continuous, linearly non-continuous surface 335 of delivery interface 10. It is presently preferred that the total length of delivery interface 10 be at least about 40 mm, more particularly from about 40 mm to about 200 mm and more particularly still, from about 40 mm to about 100 mm in length.

The segment with which the delivery interface is in contact may be afflicted with or suspected to be afflicted with the vascular disease being treated over the entire length of the contact between the surface of the delivery interface or only in certain regions of the segment. For example, although a delivery interface may be 40 mm in length, only isolated regions much less than 40 mm, e.g., as few as one or two regions that may each be as small as less than about 1 mm or greater than 1 mm but less than 40 mm, over the 40 mm interface, may actually be afflicted with the vascular disease. An important aspect of this invention, however, is that the delivery interface fully encompasses all regions of the vessel that are so afflicted and, in addition, encompasses a portion of a non-afflicted region at the periphery of the afflicted region. For example, without limitation, in a vessel having four regions afflicted or suspected to be afflicted with a vascular disease, where the most distant of the four regions are 60 mm apart, the delivery interface of this invention would be at least about 61 or 62 mm and presently preferably from about 65 mm to about 70 mm in length to fully encompass the afflicted region and a portion of the non-afflicted region at the periphery of the afflicted region.

As used herein, "contacting" a delivery interface with a surface refers to placing the delivery interface surface in contact with the luminal or adventitial surface a vessel along a regional segment of the vessel, preferably an at least about 40 mm long segment of the vessel, such that a therapeutic agent may be transferred from the delivery interface directly onto or into the surface of the vessel. By "onto the surface of the vessel" is meant that the therapeutic agent is simply released from the surface of the delivery interface and, since the surface of the delivery interface is in contact with the outer surface of the vessel, the therapeutic agent is also in contact with the outer surface, i.e., it has been delivered onto the surface of the vessel. By "into the surface of the vessel" is meant that the delivery interface includes some means such as, without limitation, micro-needles that, when the surface of the delivery interface is in contact with the surface of the vessel, penetrate the surface of the vessel and deliver the therapeutic agent into the interior of the wall of the vessel.

As used herein, "known" to be afflicted with a vascular disease refers first to a condition that is relatively readily observable and or diagnosable. An example, without limitation, of such a disease is atherosclerosis, which is a discrete narrowing of a patient's arteries. Restenosis, on the other hand, while in its latter stages, like atherosclerosis, is relatively readily diagnosable or directly observable, may not be so in its nascent stage. Thus, a patient may be "suspected" of being afflicted or of being susceptible to affliction with restenosis at some time subsequent to a surgical procedure to treat an atherosclerotic lesion. Further, while restenosis tends generally to occur at the same locus as a previous atherosclerosis, it may not be exactly so, so a region of a segment of a vessel somewhat distant from the site of the initial atherosclerosis may in fact be the site of a restenosis.

Vulnerable plaque on the other hand is quite different from either atherosclerosis or restenosis and would generally come under the designation "suspected" affliction. This is because vulnerable plaque occurs primarily within the wall of a vessel and does not cause prominent protrusions into the lumen of the vessel. It is often not until it is "too late," i.e., until after a vulnerable plaque has broken and released its components into the vessel that its presence is even known. Numerous methods have and are being investigated for the early diagnosis of vulnerable plaque but to date none have proven completely successful. Thus, the regional treatment of a segment of a vessel suspected of being afflicted with vulnerable plaque may be the best way to address such lesions.

As use herein, "delivering a therapeutic agent" refers to the transfer of the therapeutic agent from the delivery interface onto or into a surface of a vessel being treated. The transfer may be passive, as in the case, without limitation, of simple diffusion along a concentration gradient or it may be active such as when using, again without limitation, the aforementioned micro-needles through which a therapeutic agent is forceably injected into the surface or surrounding periadventitial space of a vessel.

As used herein, a "vessel wrap" refers to length of flexible material, which may be, without limitation, a fabric, a polymer, a metal and the like. The length is such that the wrap encompasses not only the afflicted region of a vessel being treated but a portion of the non-afflicted region at the periphery of the afflicted region. It is presently preferred that a vessel wrap have a length of at least about 40 mm, preferably from about 40 mm to about 200 mm and presently most preferably from about 40 mm to about 100 mm. The material is simply wrapped around the adventitial surface of a vessel such that a surface of the wrap is in intimate contact with the surface of the vessel over the entire region of the vessel known or suspected to be afflicted with a vascular disease. A therapeutic agent may be carried on the surface of the wrap, either as such or as a pharmaceutically acceptable composition or it may be located within the wrap substance, again, as such or as a pharmaceutical composition.

As used herein, a "balloon" refers to the well-known in the art device, usually associated with a vascular catheter, that comprises a relatively thin, elastomeric material that when positioned at a particular location in a patient's vessel can be expanded or inflated to an outside diameter that is essentially the same as the inside or luminal diameter of the vessel in which it is placed. The difference between the normal balloon as currently understood in the art is that the balloon of this invention achieves the diameter necessary to place it in contact with the luminal surface of the vessel over an area of the vessel that includes not only the afflicted region of the vessel but a portion of the non-afflicted region at the periphery of the afflicted region. It is presently preferred that a balloon of this invention span at least about a 40 mm, more particularly from about 40 mm to about 200 mm and more particularly still about 40 mm to about 100 mm. segment of the vessel.

Inflation of the balloon may be effected by any means known or as shall become known in the art. At present, a balloon of this invention may be inflated using a liquid medium such as water or normal saline solution, that is, saline that is essentially isotonic with blood.

Figure 5:
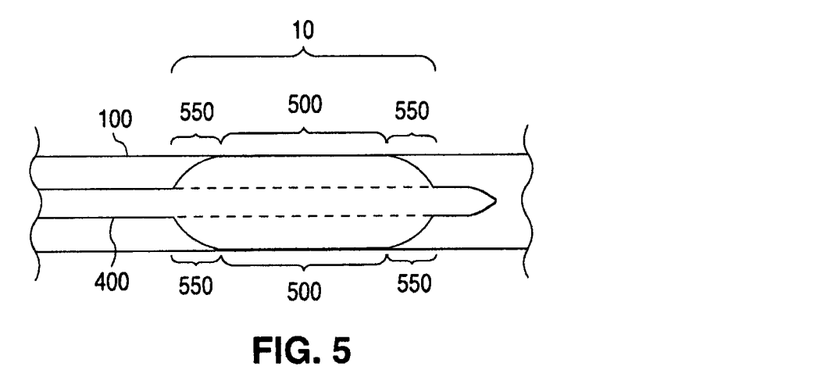
FIG. 5 is a schematic depiction of an embodiment of this invention wherein the delivery interface comprises a balloon having substantially one diameter when inflated.

A balloon of this invention may have substantially a single diameter over its entire length such that the full length of the balloon is in contact with the luminal surface of the vessel, as shown in FIG. 5. FIG. 5 also shows what is meant by "substantially" a single diameter. As can be seen in the figure, the ends 550 of balloon 520 are not necessarily square so that the balloon does have a large number of diminishing diameters at the ends at it curves down to join the catheter tube but the major portion of balloon length 500, which comprises delivery interface 10, has substantially the same diameter.

Figure 6:
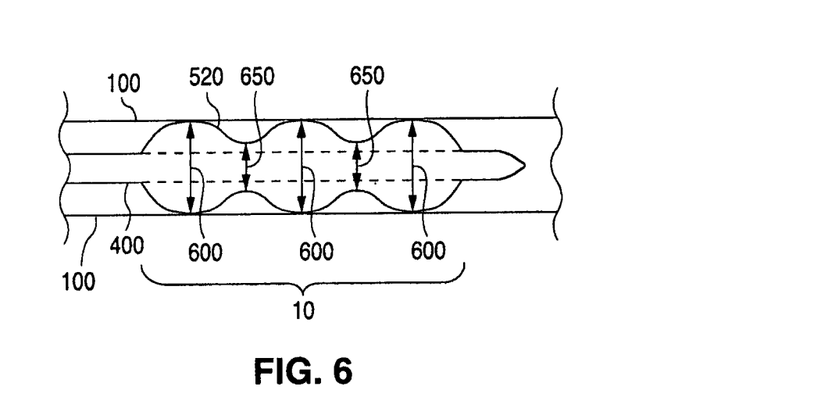
FIG. 6 is a schematic depiction of an embodiment of this invention wherein the delivery interface comprises a balloon having a first diameter that, when the balloon is inflated, contacts the surface of a vessel, and a second diameter that, when the balloon is inflated, does not contact the surface of the vessel.

A balloon of this invention may also comprise two different outside diameters. At each end of the balloon is a first diameter, which is the same as the diameter of the single diameter balloon described above; the two first diameters being sufficiently separated so as to contact non-afflicted portions of the vessel to either side of the afflicted portion. It is presently preferred that the two first diameters be at least about 40 mm, more particularly from about 40 mm to about 200 mm and, more particularly still, from about 40 mm to about 100 mm, apart. Between the end first diameters may be any number of additional first diameters. Each such first diameter is separated from each other such diameter by a second diameter which is less than the inside diameter of the vessel and therefore does not contact the luminal surface. Of course, use of the term "a second diameter" is nominal; the point is that there are regions between the first diameters that are not in contact with the luminal surface and the diameters of those regions may be identical or all may be different; for the purposes of this discussion it is assumed that they are all the same. This is illustrated in FIG. 6 wherein balloon 620 has first diameters 600, which contact vessel wall 100 and second diameters 650. which do not contact with vessel wall 100 and delivery interface 10 comprises the total length of the balloon including both diameters 600 and 650. The balloon is delivered to the selected site in the vessel by device 400, which may be, without limitation, a catheter. Depending on the design of the delivery interface, a therapeutic agent may be delivered only from those diameters that are substantially the same as the luminal diameter, the second diameters acting as spacers only. It is an aspect of this invention that therapeutic agent may be delivered directly to a luminal surface by those surfaces of the delivery interface in contact with the luminal surface; however, it is also an aspect of this invention that the therapeutic agent may as well be delivered in to the space between those surfaces; that is, from the surfaces comprising the spacer diameters. This is discussed in more detail below.

Figure 7:
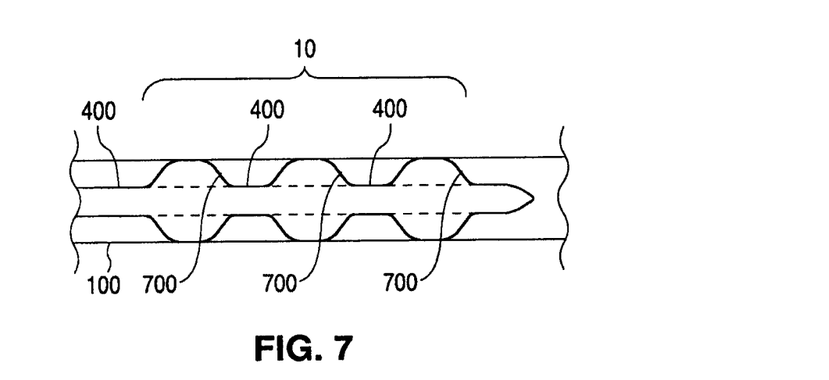
FIG. 7 is a schematic depiction of an embodiment of this invention wherein the delivery interface comprises a plurality of separate balloons.

In addition to the single diameter and dual diameter balloons, it is also an aspect of this invention to use multiple balloons each of which has substantially one diameter that is substantially the same as the luminal diameter of the vessel. The end two separate balloons must contact the luminal wall at non-afflicted portions of the vessel to either side of the afflicted portion. As above, it is presently preferred that the two balloon be at least about 40 mm, more particularly from about 40 mm to about 200 mm and, more particularly still, from about 40 mm to about 100 mm apart. Such an arrangement of balloons is illustrated in FIG. 7 where balloons 700, each of which has the same diameter, comprise delivery interface 10 and each balloon is attached to device 400, which may be, without limitation, a catheter.

A balloon of this invention may comprise a coating on all or part of its surface, the coating being the delivery interface of this invention. Coated balloons are well-known in the art for the localized delivery of therapeutic agents and any coating construct known or as may in the future become known may be used in the method of this invention with the proviso that at least two contact delivery regions of the balloon must be capable of contacting the luminal surface of the vessel in the non-afflicted region of the vessel at the periphery of the afflicted region.

Rather than or in addition to being coated, a balloon of this invention may be microporous. A microporous balloon comprises a thin membrane in which a large number; e.g., hundreds, thousands even millions of holes of substantially uniform size have been created. The holes can range in size from tens of nanometers to microns and can be created by a number of techniques including, but not limited to, laser drilling and ab initio synthesis. In the latter case, the membrane is synthesized from molecules that assemble in such a manner than voids are left in the structure formed. A microporous balloon formed by these or any other procedure may be used in the method of this invention.

When using a microporous balloon, the therapeutic agent or agents are delivered to the balloon at the distal end of a catheter in the fluid used to expand the balloon. When the balloon is expanded, rather than simply leaking out of the balloon in an uncontrolled manner, the size of the holes results in a slow, controlled "weeping" of fluid from the holes and carried along with the fluid are the therapeutic agents. The fluid and therapeutic agents then spread out over the surface of the balloon in a thin film and when the surface of the balloon is contacted with the luminal surface of a vessel, the therapeutic agents are brought into contact with the luminal surface and held there until they penetrate the surface of the vessel wall. If a balloon having two diameters as discussed above is used, only those portions of the balloon having the first diameter, that is, the portions that are in contact with the luminal surface can be microporous with the regions characterized by the second diameter are non-porous. In this case, therapeutic agent will be delivered to the luminal surface only by those regions of the balloon that are in contact with it. It is also an aspect of this invention, however, that one or more of the regions of the balloon having the second diameter can also be microporous in which case therapeutic agents will be delivered into the arterial lumen and not directly onto the luminal surface.

In another aspect of this invention, the balloon comprises micro-needles. Micro-needles, as the name implies, are exceeding small needles, often a millimeter or less in length and less than 150 microns in diameter. The micro-needles may be constructed of permanent materials such as stainless steel or they may be constructed of biodegradable polymers that exhibit thread-forming properties such that they might be attached to an implantable medical device which is left in place but from which the micro-needles eventually biodegrade and their degradation products are either adsorbed or excreted. One or a large plurality numbering in the hundreds, thousands or even more, of these micro-needles can be coupled to the surface of a balloon such that, when the balloon is deflated, the needles lie substantially parallel to the surface of the catheter tube to which they and the balloon are attached. As the balloon is being inflated the needles splay out to substantially right angles to the surface of the expanding balloon and then, when the balloon approaches a vessel surface, they are forced through the outer surface into the interior of the vessel wall.

Therapeutic agents may then be injected directly into the subsurface tissues and cells of the vessel. This can have a distinct advantage when delivering therapeutic agents to luminal wall of an artery. The inner surface of arteries comprises a layer of cells called the endothelium. The endothelium is a smooth, slippery surface designed to facilitate blood flow through the arteries. As a result, it can be difficult to get therapeutic agents past the endothelium to the underlying cells. When the endothelium is penetrated by the micro-needles, the protective outer surface of the arterial lumen is effectively by-passed and the therapeutic agent can be delivered directly into the adventia, a layer of fat and elastic fibers that surrounds and protects the artery. Compared to the endothelium, the adventitia is very receptive to therapeutic agents, which then relatively easily permeates and surrounds the cells in the vicinity of the injection.

As used herein, a "therapeutic agent" refers to a substance that, when administered to a patient has a beneficial effect on the health and well-being of the patient. Therapeutic agents may be, without limitation, small molecule drugs, large molecule drugs, peptides, antibodies, proteins, enzymes, oligonucleotides, DNAs or RNAs. Representative therapeutic agents for use with the method hereof include but are not limited to anti-inflammatory compounds, cytostatic compounds, cytokine inhibiting compounds, growth factor inhibiting compounds, enzyme inhibiting compounds, signaling pathway inhibiting compounds and cytotoxic compounds.

A presently preferred therapeutic agent for use in the method of this invention is apolipoprotein A1 (apoA1), apoA1 mutants such as, without limitation, apoA1-milano or apoA1 mimetics such as, again without limitation, amphipathic helical peptides. ApoA1 is synthesized in the liver and small intestine and is the primary protein constituent of high density lipoprotein (HDL), making up 70% of the latter. ApoA1 is responsible for most of HDL's defining characteristics including its participation in reverse cholesterol transport. That is, apoA1 defines the size and shape of the HDL molecule: discoid in its nascent stage, consisting of a phosphatidylcholine bilayer and a protein shell that shields the hydrophobic lipid tails from the aqueous environment, and spherical in its mature form, consisting of a hydrophobic core of cholesterol esters shielded by a combination of lipid and protein. When mature, HDLs cease to collect cholesterol and are recognized by the liver for excretion. ApoA1 is also responsible for solubilizing of HDL's lipid components, removing cholesterol from peripheral cells, activating lecithin-cholesterol acyl transferase (LCAT) enzyme and delivering the resulting cholesterol esters to the liver.

Cholesterol is a major component of atherosclerotic plaque. Cholesterol accumulates in the arterial wall as the result of the influx of lipoproteins containing apoB. When influx exceeds natural efflux, artherosclerotic plaque begins to form. Reverse cholesterol transport refers to the active efflux and transportation to the liver for excretion of cholesterol from arterial walls to counter the influx from the apoB-containing lipoproteins. While increased levels of HDL have been known for some time to correlate with a decreased risk of atherosclerosis, it has recently been demonstrated that purified apoA1 is capable of reducing free cholesterol accumulation in vivo in atherosclerotic lesions. (Boisvert, W. A., et al., *Arteriosclerosis, Thrombosis, and Vascular Biology*, 1999, 19:525-530). Thus, vessels known or suspected to be either accumulating cholesterol as the result of influx exceeding efflux or to actually be afflicted with atherosclerotic lesions as the result of such accumulation should benefit from the regional administration of apoA1 using the method of this invention.

ApoA1 is a relatively large protein consisting of 243 amino acids. The problems associated with working with such large proteins in terms of stability, bioavailability, etc. are well-known. It would be preferable to use apoA1 mimetic peptides having substantially less amino acids. One such apoA1 mimetic peptide has been reported, an 18-mer that has been shown to promote reverse cholesterol transport in cultured cholesterol-laden fibroblasts and macrophages and to interact with cell surface HDL binding sites thereby stimulating an HDL-like response. Mendez, A. J., et al, *J. Clin. Invest.*, 1994, 94:1698-1705. Other such apoA1 mimetics are being actively sought (see for instance, Mishra, V. K., *Biochemistry*, 1998, 37:10313-324) and any such compounds discovered would be expected to provide a beneficial effect as a therapeutic agent administered regionally by means of a delivery interface of this invention.

A presently preferred family of therapeutic agents useful in the method of this invention is the bisphosphonates. Bisphosphonates are known to induce apoptosis in macrophages. Apoptosis is best described as a sort of cell suicide whereby specialized cellular machinery already present in the cell but previously quiescent is activated, causing the cell to disintegrate into fragments that are then eliminated from the organism containing the cell. Macrophages are phagocytotic tissue cells of the reticuloendothelial system that ingest, by engulfing or "cytosing," foreign substances such as bacteria, cellular debris, viruses, toxins, particulates, etc. Thus macrophages are important to the health and well-being of humans, With regard to the above-described increased influx of cholesterol into the arterial wall, however, which is accompanied by an increased influx of monocytes/macarophages (monocytes differentiate into macrophages) that take up oxidized and aggregated low density lipoprotein (LDL) and store the cholesterol as esters, macrophages perform a disservice to the system. That is, whereas parenchymal cells maintain cholesterol balance by down-regulating de novo cholesterol synthesis and LDL receptor expression, macrophages continue to take up cholesterol from apoB-containing lipoproteins by pathways that are not subject to sterol-mediated feedback control. Spady, *Circulation*, 1999, 576-78. In addition to accumulating cholesterol, macrophages play a role in inducing plaque rupture, blood coagulation and fibrinolysis through the production of various enzymes, activators, inhibitors and therapeutic mediators. Takahashi, et al., *Med. Electron Microsc.*, 2002, 35(4):179-203. Thus, in the context of vascular disease, the presence of macrophages is undesirable and their elimination from vessels known or suspected to be accumulating cholesterol and therefore to likely be pre-atherosclerotic or in vessels that in fact contain atherosclerotic lesions by regional delivery of bisphosphonates should be of benefit to patients so afflicted.

Bisphosphonates have the general structure:

Bisphosphonates useful in the method of this invention include, but are not limited to, etidronate ($R^1$=OH, $R^2$=$CH_3$), chlodronate ($R^1$=$R^2$=Cl), tiludronate ($R^1$=OH, $R^2$=4-chlorophenylmercapto), pamidronate ($R^1$=OH, $R^2$=2-aminoethyl), olpadronate (dimethyl pamidronate, $R^1$=OH, $R^2$=N,N-dimethyl-2-aminoethyl), alendronate ($R^1$=OH, $R^2$=3-aminopropyl), ibandronate ($R^1$=OH, $R^2$=N-methyl, N-ethyl-2-aminoethyl), risedronate ($R^1$=OH, $R^2$=3-pyridinylmethyl), minodronate ($R^1$=OH, $R^2$=4-azaindole-3-methyl) and zoledronate ($R^1$=OH, $R^2$=1-imidazolylmethyl).

While for some time considered to be simply a lipid storage disease, recent studies have demonstrated that atherosclerosis actually involves an on-going inflammatory response. In fact inflammation has been established as having a fundamental role in mediating virtually all stages of the disease from initiation through progression and ultimately to the thrombotic complications associated with atherosclerosis. For example, blood leukocytes, mediators of host defenses and inflammation, have been shown to localize in the earliest lesions of atherosclerosis. The normal endothelium does not in general support binding of white blood cells but in the early stages of atherosclerosis patches of arterial endothelial cells have been observed to express on their surface selective adhesion molecules that bind to various classes of leukocytes. In particular expression of vascular cell adhesions molecule-1 (VCAM-1) has been observed on endothelial cells overlying nascent atheroma. VCAM-1 binds both monocytes (macrophage precursors) and T lympocytes, both of which are involved in inflammatory responses. Libby, et al., *Circulation*, 2002, 105:1135. Thus, another presently preferred family of therapeutic agents for use in the method of this invention are the anti-inflammatory agents. Anti-inflammatory agents useful herein include, but are not limited to, statins, corticosteroids, and antioxidants.

A presently preferred class of anti-inflammatory agents for use in the method of this invention is the statins. Statins are of particular interest because of their potential dual role in the treatment of atherosclerosis. That is, the primary function for which they are generally prescribed is to lower the production of cholesterol by the liver by blocking the enzyme 3-hydroxy-3-methylglutaryl-coenzyme A reductase (HMG-CoA reductase) A. As noted above, cholesterol plays a key role in the formation of atherosclerotic lesions so a reduction in its production should be a major benefit to patients susceptible to or afflicted with atherosclerosis. The results of many clinical studies, however, have shown the improvement in cardiovascular risk reduction obtained from the administration of statins to be superior to the estimations calculated from the effect on LDL cholesterol lowering. Recent studies have shown that statins have an inhibitory effect on the monocyte-endothelial interaction discussed above suggesting an anti-inflammatory effect as well as a cholesterol lowering effect. Thus the statins should have a marked beneficial effect when administered regionally using the method of this invention. Useful statins include, but are not limited to, atorvastatin (Lipitor®), lovastatin (Mevacor®), simvastatin (Zocor®), fluvastatin (Lescol®) and pravastatin (Pravachol®).

Another class of presently preferred therapeutic agents for use in the method of this invention is the corticosteroids. Corticosteroids include cortisol, an adrenal hormone found naturally in the body, as well as synthetic drugs. They all are potent anti-inflammatory compounds with the synthetic corticosteroids exerting the strongest effects. Corticosteroids potentially useful in the method of this invention include, but are not limited to, alclometasaone, amcinonide, betamethasone, clobestasole, clocortalone, desonide, desoxymetasone, diflorasone, flucinolone, fluocinonide, flurandrenolide, fluticasone, halcinonide, halobetasol, hydrocortisone, methylprednisolone, mometasoneprednicarbate, triamcinolone. Presently particularly preferred corticosteroids for use herein are clobestesol and desoxymetasone.

Additional therapeutic agents that are presently preferred for use in the method of this invention are rapamycin and its analogs, sirolimus, biolimus, everolimus, paclitaxel and 17-allylamino-17-demethoxygelanamycin (17-AAG).

Of course, a host of other therapeutic agents may be incorporated into the method of this invention as their use is developed, expanded and found to be applicable to the diseases and disorders treatable using regional delivery. Such therapeutic agents include, without limitation, synthetic inorganic and organic compounds, proteins and peptides, polysaccharides and other sugars, lipids, DNA and RNA nucleic acid sequences including siRNA, antisense oligonucleotides, antibodies, receptor ligands, enzymes, adhesion peptides, blood clot agents such as streptokinase and tissue plasminogen activator, antigens, hormones, growth factors, ribozymes, retroviral vectors, anti-proliferative agents such as rapamycin (sirolimus), 40-O-(2-hydroxyethyl)rapamycin (everolimus), 40-O-(3-hydroxypropyl)rapamycin, 40-O-(2-hydroxyethoxy)ethylrapamycin, 40-O-tetrazolylrapamycin (zotarolimus, ABT-578), paclitaxel, docetaxel, methotrexate, azathioprine, vincristine, vinblastine, fluorouracil, doxorubicin hydrochloride, mitomycin, antiplatelet compounds, anticoagulants, antifibrin, antithrombins such as sodium heparin, low molecular weight heparins, heparinoids, hirudin, argatroban, forskolin, vapiprost, curcumin, fingolimandod (FTY-720), prostacyclin, prostacyclin analogues, dextran, D-phepro-arg-chloromethylketone (synthetic antithrombin), dipyridamole, glycoprotein IIb/IIIa platelet membrane receptor antagonist antibody, recombinant hirudin, thrombin inhibitors such as Angiomax ä, calcium channel blockers such as nifedipine, colchicine, fibroblast growth factor (FGF) antagonists, fish oil (omega 3-fatty acid), histamine antagonists, lovastatin, monoclonal antibodies, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, estradiol, anticancer agents, dietary supplements such as vitamins, anti-inflammatory agents such as aspirin, tacrolimus, dexamethasone and clobetasol, cytostatic substances such as angiopeptin, angiotensin converting enzyme inhibitors such as captopril, cilazapril or lisinopril, antiallergic agents is permirolast potassium, alpha-interferon, bioactive RGD, and genetically engineered epithelial cells.

Activation of immune cells and unregulated proliferation and motility of vascular smooth muscle cells are known to contribute to neointimal lesion development during the pathogenesis of atherosclerosis and restenosis. Vascular smooth muscle cells migrate from the sub-endothelium into the arterial wall intimal layer where they proliferate and lay down an extracellular matrix that causes vascular wall thickening and reduced vessel patency. Thus, inhibition of this process would be expected then to have a salutary effect in a vessel afflicted with or suspected to be afflicted with actual or nascent atherosclerotic or restenotic lesion(s). Rapamycin, also known as sirolimus, is a macrolide compound which has been shown to have antiproliferative activity toward smooth muscle cells and to inhibit neointimal formation. Thus sirolimus would be expected to be a beneficial therapeutic agent for use with the method of this invention.

Everolimus, (40-O-2-hydroxyethylrapamycin), has, however, has better pharmacokinetics that sirolimus; i.e., a shorter half-life, a higher bioavailability and a stronger correlation between bioavailability and administered dose. Thus, while structurally similar, everolimus is presently preferred over sirolimus for use in the method of this invention.

Geldanamycin, a benzoquinone ansamycin isolated from *Streptomyces hygroscopicus* in the early 1970s, has developed into a promising chemotherapeutic with activity against a number of cancers. One of its analogs, 17-allylamino-17-desmethoxygeldanamycin (17-AAG) is more stable and less toxic than the parent compound and appears to be an equally potent chemotherapeutic. Both geldanamycin and 17-AAG bind to heat shock protein 90 (Hsp90) and alter its function. Hsp90 plays a key role in regulating the physiology of cells exposed to environmental stress and in maintaining the malignant phenotype of tumor cells. In addition, Hsp90 participates in the regulation of the cell cycle, cell growth, cell survival and apoptosis. Geldanamycin and 17-AAG bind to the ATP-binding pocket of Hsp-90 and induce degradation of proteins that require this chaperone for conformational maturation. More recently, 17-AAG has been shown to be selectively anti-proliferative toward smooth muscle cells and not endothelial cells and is being investigated as a potential inhibitor of restenosis and therefore would be expected to have a beneficial effect in patients being treated using the method herein.

The therapeutic agent herein may be provided simply as particles or a film of the agent adhered to the surface of the delivery interface. Or it may be provided as a solution or suspension of the agent in a polymeric matrix adhered to the surface of a delivery interface of this invention. Or it may be provided as a pharmaceutically acceptable composition adhered to the surface of the delivery interface or entrapped in a polymeric matrix adhered to the surface of the delivery interface. A "pharmaceutically acceptable composition" refers to composition that does not cause significant irritation to an organism to which it is administered and does not abrogate the biological activity and properties of the therapeutic agent. In particular, pharmaceutically acceptable compositions for use in the methods of this invention comprise encapsulation of the therapeutic agent in a pharmaceutically acceptable carrier. Examples of pharmaceutically acceptable carriers include but are not limited to micelle encapsulated therapeutic agent, liposome encapsulated therapeutic agent, polymerosome encapsulated therapeutic agent, therapeutic agent encapsulated in polymeric micro- or nanoparticles, preferably in particles comprising biodegradable or bioerodable polymer, therapeutic agent encapsulated in micro- or nanoparticles comprising porous glass and/or silica, preferably in particles comprising biodegradable or bioerodable glass and/or silica, therapeutic agent encapsulated in porous metal micro- or nanoparticles, preferably in particles comprising biodegradable or bioerodable metal. water-in-oil emulsions of therapeutic agent, oil-in-water emulsions of therapeutic agent, water-in-oil-in-water emulsions of therapeutic agent and oil-in-water-in-oil emulsions of therapeutic agent.

An example, without limitation, of a therapeutic agent being provided simply as a solution and being administered regionally in that form by means of a delivery interface of this invention would be the dissolution of a water-soluble bisphosphonate, a di-sodium or ammonium salt for instance, in water or isotonic saline and delivery by means of a microporous balloon as described above. Generally, the therapeutic agent must be soluble in water or saline for this means of delivery to be useful because other solvents may have a deleterious effect on the vessel at the point of delivery. Since many, if not most, therapeutic agents are generally poorly soluble in water, the utility of this means of delivery is somewhat limited.

For therapeutic agents that are minimally water soluble, the means of administration may comprise a suspension of the therapeutic agent in a polymeric matrix which is applied to the surface of a device such as, without limitation, a balloon or stent, which will be in contact with the wall of a vessel. As such the polymer/therapeutic agent layer becomes the delivery interface of this invention. Any polymer presently known in the art or as such may become known in the future may be used for this mode of administration. A few non-limiting examples are poly(L-lactide), poly(D-lactide), poly(D,L-lactide), poly(meso-lactide), polyglycolide, poly(L-lactide-co-D,L-lactide), poly(L-lactide-co-glycolide), poly(D-lactide-co-glycolide), poly(D,L-lactide-co-glycolide), poly(meso-lactide-co-glycolide), poly(caprolactone), poly (hydroxyvalerate), poly(hydroxybutyrate), poly(ester amide), poly(ethylene glycol-co-butylene terephthalate)

(POLYACTIVE®), polycaprolactone (PCL), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly(amino acids), cyanoacrylates, poly(trimethylene carbonate), poly(iminocarbonate), copoly(ether-esters), polyalkylene oxalates, polyphosphazenes, polyiminocarbonates, polycarbonates, fibrin, fibrinogen, cellulose, starch, collagen, parylene, polyurethane, polyethylene, polyethylene teraphthalate, ethylene vinyl acetate, silicone, polyethylene oxide, poly(ethylene-co-vinyl alcohol), polyesters, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose and mixtures thereof.

In the alternative, when a therapeutic agent is poorly soluble an effective pharmaceutically acceptable composition can be a micelle. A micelle is a spherical colloidal nanoparticle spontaneous formed by many amphiphilic molecules in an aqueous medium when the Critical Micelle Concentration (CMC) is exceeded. Amphiphilic molecules have two distinct components, differing in their affinity for a solute, most particularly water. The part of the molecule that has an affinity for water, a polar solute, is said to be hydrophilic. The part of the molecule that has an affinity for non-polar solutes such as hydrocarbons is said to be hydrophobic. When amphiphilic molecules are placed in water, the hydrophilic moiety seeks to interact with the water while the hydrophobic moiety seeks to avoid the water. To accomplish this, the hydrophilic moiety remains in the water while the hydrophobic moiety is held above the surface of the water in the air or in a non-polar, non-miscible liquid floating on the water. The presence of this layer of molecules at the water's surface disrupts the cohesive energy at the surface and lowers surface tension. Amphiphilic molecules that have this effect are known as "surfactants." Only so many surfactant molecules can align as just described at the water/air or water/hydrocarbon interface. When the interface becomes so crowded with surfactant molecules that no more can fit in, i.e., when the CMC is reached, any remaining surfactant molecules will form into spheres with the hydrophilic ends of the molecules facing out, that is, in contact with the water forming the micelle corona and with the hydrophobic "tails" facing toward the center of the of the sphere. Therapeutic agents suspended in the aqueous medium can be entrapped and solubilized in the hydrophobic center of micelles which can result in an increase in the bioavailability as well as improving the stability in biological surroundings, improving the pharmacokinetics and possibly decreasing the toxicity of the therapeutic agent. In addition because of their nanoscale size, generally from about 5 nm to about 50 nm, micelles have been shown to exhibit spontaneous accumulation in pathological areas with leaky vasculature and impaired lymphatic drainage, a phenomenon known as the Enhanced Permeability and Retention or EPR effect.

The problem with micelles formed from relatively low molecular weight surfactants is that their CMC is usually quite high so that the formed micelles dissociate rather rapidly upon dilution, i.e., the molecules head for open places at the surface of the water with the resulting precipitation of the therapeutic agent. Fortunately, this short-coming can be avoided by using lipids with a long fatty acid chain or two fatty acid chains, specifically phospholipids and sphingolipids, or polymers, specifically block copolymers to form the micelles.

Polymeric micelles have been prepared that exhibit CMCs as low as $10^{-6}$ M (molar). Thus, they tend to be very stable while at the same time showing the same beneficial characteristics as surfactant micelles. Any micelle-forming polymer presently known in the art or as such may become known in the future may be used in the method of this invention. Since micelles are nano-scale particles, they may be administered using the porous balloon discussed above as well as in polymeric matrices. Examples of micelle-forming polymers are, without limitation, methoxy poly(ethylene glycol)-b-poly(ε-caprolactone), conjugates of poly(ethylene glycol) with phosphatidylethanolamine, poly(ethylene glycol)-b-polyesters, poly(ethylene glycol)-b-poly(L-aminoacids), poly(N-vinylpyrrolidone)-bl-poly(orthoesters), poly(N-vinylpyrrolidone)-b-polyanhydrides and poly(N-vinylpyrrolidone)-b-poly(alkyl acrylates).

In addition to the classical spherical micelles described above, therapeutic agents may be delivered using the methods of this invention in compositions comprising synthetic worm micelles. Worm micelles, as the name suggests, are cylindrical in shape rather than spherical. They are prepared by varying the weight fraction of the hydrophilic polymer block to the total block copolymer molecular weight in the hydrophilic polymer-b-hydrophobic polymer structure discussed above for preparing spherical micelles. Worm micelles have the potential advantage of not only being bio-inert and stable as are spherical polymeric micelles but also of being flexible. Polyethylene oxide has been used extensively to create worm micelles with a number of hydrophobic polymers such as, without limitation, poly(lactic acid), poly(ε-caprolactone), poly(ethylethylene) and polybutadiene. A representative description of worm micelle formation, characterization and drug loading can be found in Kim, Y., et al., *Nanotechnology*, 2005, 16:S484-S491. The techniques described there as well an any other that is currently known or may become known in the future may be used in the regional delivery method of this invention. In addition to compositions comprising micelles, therapeutic agents may be present in or on a delivery interface of this invention as a composition comprising liposomes.

Phospholipids are molecules that have two primary regions, a hydrophilic head region comprised of a phosphate of an organic molecule and one or more hydrophobic fatty acid tails. In particular, naturally-occurring phospholipids have a hydrophilic region comprised of choline, glycerol and a phosphate and two hydrophobic regions comprised of fatty acid. When phospholipids are placed in an aqueous environment, the hydrophilic heads come together in a linear configuration with their hydrophobic tails aligned essentially parallel to one another. A second line of molecules then aligns tail-to-tail with the first line as the hydrophobic tails attempt to avoid the aqueous environment. To achieve maximum avoidance of contact with the aqueous environment, i.e., at the edges of the bilayers, while at the same time minimizing the surface area to volume ratio and thereby achieve a minimal energy conformation, the two lines of phospholipids, know as a phospholipid bilayer or a lamella, converge into a sphere and in doing so entrap some of the aqueous medium, and whatever may be dissolved or suspended in it, in the core of the sphere. Examples of phospholipids that may be used to create liposomes are, without limitation, 1,2-dimyristroyl-sn-glycero-3-phosphocholine, 1,2-dilauroyl-sn-glycero-3-phosphocholine, 1,2-distearoyl-sn-glycero-3-phosphocholine, 1,2-dimyristoyl-sn-glycero-3-phosphoethanolamine, 1,2-dipalmitoyl-sn-glycero-3-phosphoethanolamine, 1,2-dioleoyl-sn-glycero-3-phosphate monosodium salt, 1,2-dipalmitoyl-sn-glycero-3-[phosphor-rac-(1-glycerol)]sodium salt, 1,2-dimyristoyl-sn-glycero-3-[phospho-L-serine]sodium salt, 1,2-dioleoyl-sn-glycero-3-phosphoethanolamine-N-glutaryl sodium salt and 1,1',2,2'-tetramyristoyl cardiolipin ammonium salt.

Liposomes may be unilamellar, composed of a single bilayer, or they may be multilamellar, composed of two or more concentric bilayers. Liposomes range from about 20-100 nm diameter for small unilamellar vesicles (SUVs), about 100-5000 nm for large multilamellar vesicles and ultimately to about 100 microns for giant multilamellar vesicles (GMVs). LMVs form spontaneously upon hydration with agitation of dry lipid films/cakes which are generally formed by dissolving a lipid in an organic solvent, coating a vessel wall with the solution and evaporating the solvent. Energy is then applied to convert the LMVs to SUVs, LUVs, etc. The energy can be in the form of, without limitation, sonication, high pressure, elevated temperatures and extrusion to provide smaller single and multi-lamellar vesicles. During this process some of the aqueous medium is entrapped in the vesicle. Generally, however, the fraction of total solute and therefore the amount of therapeutic agent entrapped tends to be rather low, typically in the range of a few percent. Recently, however, liposome preparation by emulsion templating (Pautot, et al., *Langmuir*, 2003, 19:2870) has been shown to result in the entrapment of virtually 100% of aqueous solute. Emulsion templating comprises, in brief, the preparation of a water-in-oil emulsion stabilized by a lipid, layering of the emulsion onto an aqueous phase, centrifugation of the water/oil droplets into the water phase and removal of the oil phase to give a dispersion of unilamellar liposomes. This method can be used to make asymmetric liposomes in which the inner and outer monolayers of the single bilayer contain different lipids. Any of the preceding techniques as well as any others known in the art or as may become known in the future may be used as compositions of therapeutic agents in or on a delivery interface of this invention. Liposomes comprising phospho- and/or sphingolipids may be used to deliver hydrophilic (water-soluble) or precipitated therapeutic compounds encapsulated within the inner liposomal volume and/or to deliver hydrophobic therapeutic agents dispersed within the hydrophobic core of the bilayer membrane.

It has been reported that large unilamellar liposomes alone, that is, absent any additional therapeutic agent, when administered in large amounts intravenously may stimulate reverse cholesterol transport and may have anti-atherogenic effects similar to that of HDL. Williams, K. J., et al., *Arterioscler. Thromb. Vasc. Biol.*, 2000, 20:1033-39. While further evaluation is necessary, if such is proven to be the case, administration of large liposomes without added therapeutic agent using the delivery interface of this invention may provide a beneficial effect on patients known or suspected to be afflicted with a vascular disease.

The diblock copolymers discussed above with regard to micelle formation can be further modified to form bilayer structures similar to liposomes. The structures are referred to as polymerosomes. Depending on the length and chemical nature of the polymers in the diblock copolymer, polymerosomes can be substantially more robust that liposomes. In addition, the ability to control completely the chemical nature of each block of the diblock copolymer permits tuning of the polymerosome's composition to fit the desired application. For example, membrane thickness can be controlled by varying the degree of polymerization of the individual blocks. Adjusting the glass transition temperatures of the blocks will affect the fluidity and therefore the permeability of the membrane. Even the mechanism of release can be modified by altering the nature of the polymers.

Polymerosomes can be prepared in the same manner as liposomes. That is, a film of the diblock copolymer can be formed by dissolving the copolymer in an organic solvent, applying a film of the copolymer-containing solvent to a vessel surface, removing the solvent to leave a film of the copolymer and then hydrating the film. This procedure, however, tends to result is a polydispersion of micelles, worm micelles and vesicles of varying sizes. Polymerosomes can also be prepared by dissolving the diblock copolymer in a solvent and then adding a poor solvent for one of the blocks, which will result in the spontaneous formation of polymerosomes.

As with liposomes, polymerosomes can be used to encapsulate therapeutic agents by including the therapeutic agent in the water used to rehydrate the copolymer film. Polymerosomes can also be force-loaded by osmotically driving the therapeutic agent into the core of the vesicle. Also as with liposomes, the loading efficiency is generally low. Recently, however, a technique has been reported that provides polymerosomes of relative monodispersivity and high loading efficiency; generation of polymerisomes from double emulsions. Lorenceau, et al., *Langmuir*, 2005, 21:9183-86. The technique involves the use of microfluidic technology to generate double emulsions consisting of water droplets surrounded by a layer of organic solvent. These droplet-in-a-drop structures are then dispersed in a continuous water phase. The diblock copolymer is dissolved in the organic solvent and self-assembles into proto-polymerosomes on the concentric interfaces of the double emulsion. The actual polymerosomes are formed by completely evaporating the organic solvent from the shell. By this procedure the size of the polymerosomes can be finely controlled and, in addition, the ability to maintain complete separation of the internal fluids from the external fluid throughout the process allows extremely efficient encapsulation. This technique along with any other technique know in the art or as may become known in the future can be used to prepare a composition of therapeutic agents for use in or on a delivery interface of this invention.

In addition to the preceding membrane enclosed shell structures for the encapsulation of therapeutic agents for use with the delivery interface of this invention, a therapeutic agent may also be entrapped in water-in-oil (WO), an oil-in-water (OW), a water-in-oil-in-water (WOW) or an oil-in-water-in-oil (OWO) emulsion.

An emulsion is simply a dispersion of droplets of a liquid in a second liquid where the liquids are immiscible. Whether a WO or an OW forms from a mixture of water and oil depends to some extent on the volume fraction of each phase but more so on the type of surfactant (sometimes called an emulsifier) used. That is, according to Bancroft's Rule, the phase in which an emulsifier is more soluble will constitute the continuous phase. Which phase a particular emulsifier will be more soluble in is determined by its hydrophilic-lipophilic balance (HLB) number. HLB by definition range from 1-20.

Emulsifiers with a low HLB (i.e., one that is more soluble in oil that in water) will tend to give a WO, while emulsifiers with a high HLB will give OWs. Some common emulsifiers and their HLBs are, without limitation, acetylated monoglycerides (1.5), sorbitan trioleate (1.8), polyethyleneglycol monostearate (3.4), sorbitan monostearate (4.7), soy lecithin (8.0, polyoxyethylene(20) sorbitan 10.5 and sucrose monolaurate (15.0). Many other surfactants potentially useful for the formation of WOs and OWs are known in the art and any that is pharmaceutically acceptable may be used to prepare composition of therapeutic agents for use with a delivery interface of this invention. For example, the following are emulsifiers listed as GRAS (generally regarded as safe) by the FDA: diacetyl tartaric acid ester of mono- and di-glycerides, glycerol monostearate, glycerol monooleate, glycerol behenate, lecitihin and monosodium phosphate derivatives of mono and di-glycerides. Still other emulsifiers include, without limitation, phosphatidyl choline, stearylamine, deoxycholic acid and polyvinyl alcohol.

The lipid phase of an emulsion may comprise any number of hydrophobic materials well-known to those skilled in the art. Among these, without limitation, are such substances as isopropyl myristate, soybean oil, garlic oil and coconut oil.

If desired, an emulsion may be stabilized by incorporation of finely divided inorganic particles of materials such as, without limitation, carbon, silica or clay in the dispersion (called a Pickering emulsion). The particles adsorb to the surface of the droplets of the dispersed phase, thereby discouraging coalescence of droplets and thus stabilize the emulsion.

If desired, viscosity enhancers such as, without limitation, polyethylene oxide (PEO 50K), hyaluronic acid or polyvinylpyrrolidone can be used.

Droplet sizes in emulsions can vary from nano- to macro-scale, i.e., from about 10 nanometers (nm) to 100 nm (a nanoemulsion), about 100 nm (0.1 micron) to 100 microns (a microemulsions) or from about 100 microns to as much as 10 mm (a macroemulsion) in diameter. Droplet size can be controlled by the use of a homogenizer, a device having a very small tube through which the droplets are forced, the larger ones being distorted such that, upon emergence from the tube they can be shaken apart to form smaller droplets. Other techniques and devices are well-known in the art and may be used to prepare emulsions of an appropriate size for use with the delivery interface of this invention. In general droplets in the submicron diameter range are presently preferred although larger droplets may be used if desired.

In addition to WO and OW emulsions, therapeutic agents may be formulated as WOW or OWO emulsions. WOW/OWO emulsions are also called double emulsions because they consist of droplets of one liquid encased in a second immiscible liquid that in turn is dispersed a third liquid that is immiscible with the second liquid; e.g., water-in-oil-in-water or oil-in-water-in-oil. Double emulsions can be prepared by a variety of mixing techniques or by forcing single emulsions through membranes or nozzles. The size distribution of the droplets tends to be quite dispersed which can limit the utility of such emulsions for pharmaceutical applications. Recently, however, microfluidics has been used to create double emulsions of precisely controlled droplet size. The technique consists of a series of T-junctions through which the various liquids are forced. For example, to create a WOW, junctions were designed so that the water flowed into a channel through which oil was flowing where it was pinched off to form a WO. The WO emulsion was then directed into a second channel through which water was flowing thus creating the water-in-oil-in-water double emulsion. Utada, A. S., et al., *Science*, 2005, 308(5721):537-41.

In addition to WO, OW, WOW and OWO emulsions, a therapeutic agent for use with the delivery interface of this invention may comprise a coacervate. Coacervation is a colloidal phenomenon involving the separation of a colloidal system into two liquid phases. The phase more concentrated in colloidal component is the coacervate while the other phase is the equilibrium solution. When the coacervate is brought in contact with a core material, that is, a material to be encapsulated, the coacervate spontaneously forms a shell around the core material resulting in the formation of a microcapsule. In general, coacervation involves the mixing together under constant agitation of a core material (therapeutic agent) in a liquid in which the core material is not, or is minimally, soluble. A second solvent containing the coating material, which is likewise not soluble in the first liquid is added upon which the coating material is deposited around the core material forming a shell. The shell can be "hardened" by various means such as thermal treatment or desolvation.

While any therapeutic agent useful in the treatment or prevention of vascular disease may be administered in any one of the preceding encapsulated forms, bisphosphonates are particularly amenable to such delivery techniques. This is because it has long been known that liposomes containing bisphosphonate are readily engulfed by macrophages whereupon the liposomes are decomposed by resulting in the release of the bisphosphonate which then inactivates and/or limits the growth of the macrophage (e.g., see Monkkonen, J., et al., *J. Drug Target.*, 2003, 11(5):279-86). It has been reported that the critical size range for phagocytosis-induced macrophage activation is about 0.2 to about 10 µm, a range which each of the above-described encapsulation techniques is capable of achieving. Thus, in addition to liposomes as delivery vehicles for bisphosphonates to macrophages, each of the other compositions discussed above should likewise affect the same macrophage activation with the same result.

As noted previously, as part of their normal function macrophages engulf and destroy solid particulates such as cell debris and the like. Thus, particulate bisphosphonates should be cytosed by macrophages and should have the same effect once in the macrophage as liposome-transported bisphosphonate. Thus, insoluble particulate bisphosphonates are also pharmaceutically acceptable compositions for use with the delivery interface of this invention. In particular, it has been reported that high concentrations of extracellular calcium enhances the potency of bisphosphonates against macrophage-type cells (Monkennon, J., et al., *J. Drug Target.,* 1994, 2(4):299-308). Bisphosphonates are known calcium scavengers so it is most likely that in the presence of extracellular calcium the insoluble calcium salt of the bisphosphonate is formed, thus it is presently preferred that the insoluble bisphosphonate composition for use herein is a calcium salt, in particular the dicalcium salt.

While the insoluble particle can be a calcium salt of a synthetic bisphosphonate, it is also an aspect of this invention that naturally-occurring calcium phosphate minerals can serve as a pharmaceutically acceptable composition for use with a delivery interface hereof. Such minerals include, without limitation, brushite, octacalcium phosphate, monetite, whitlocktite, tricalcium phosphate and hydroxyapatite. Of these, hydroxyapatite is presently preferred.

It is also possible, and an aspect of this invention, to load liposomes with insoluble calcium bisphosphonate particles. The technique involves the loading of liposomes with calcium ions by any number of known means such as, without limitation, that described in Messersmith, P. B., et al., *Chem. Mater.*, 1998, 10:109-16. There a soluble bisphosphonate that is capable of crossing the liposomal lamella, for example without limitation, an ammonium salt, is introduced into the system and bisphosphonate anion is transported across the lamella. Once in the core of the liposome, the soluble bisphosphonate reacts with the calcium ions present and precipitates. When the lamella of the liposome is destroyed by a macrophage the calcium bisphosphonate is released and can affect the macrophage as discussed above.

An advantage of filing a liposome or other encapsulating shell-type carrier with an insoluble salt of a bioactive such as a bisphosphonate is improved shelf life of the resulting delivery system. That is, micelles, liposomes and to some extent polymerosomes are susceptible to loss of small molecule encapsulated therapeutic agent as it slowly leaks through the membrane of the capsule. If the therapeutic agent is precipitated within the capsule, the precipitate particle size would be expected to be too large to transgress the membrane or at least large enough to significantly reduce the rate of leakage.

In addition to actual precipitates, small molecule therapeutic agents with acidic functionality might also be rendered less likely to leak from shell-type carriers by making a salt of the therapeutic agent with a relatively bulky counter-ion. An example of such a counter-ion is, without limitation, an ammonium salt having the chemical structure:

wherein $R_1$, $R_2$, $R_3$ and $R_4$ may be the same or different and are selected from groups that will provide the requisite bulkiness. Examples of such groups include, without limitation, straight or branched chain alkyl groups, in particular at present groups such at t-butyl, optionally substituted aralkyl groups (aryl-Y— where aryl refers to a ring or two or more fused rings having a fully delocalized π-electron system and Y is an alkyl group) wherein the optional substituent increases the bulk of the molecule without adding reactivity, e.g., a straight chain or branched alkyl group, an optionally substituted alicyclic group (a ring or two or more fused rings that does not contain a fully delocalized π-electron system and a polymeric unit such as polyethylene glycol. Other such bulk-enhancing groups will be immediately evident to those skilled in the art based on the disclosure herein.

Another approach to limiting loss of a therapeutic agent from a shell-forming carriers would be the use of counter-ions consisting of two or more positively charged regions, i.e., having the chemical structure:

wherein $R_1$, $R_2$ and $R_3$ have the same meaning as set forth above and M is virtually any type of separator entity imaginable. For example, without limitation, 4,4'-bismethylenebiphenyl, polyethylene glycol, any alkylene (—Y—, where Y is a straight or branched chain alkyl group), 1,4-cyclohexyl, etc.

This approach would be expected to particularly useful with divalent therapeutic agents such as the bisphosphonates discussed above.

Coacervates of bisphosphonates may also be used as pharmaceutically acceptable compositions for regional delivery of a therapeutic agent using a delivery interface of this invention. While any coacervate known in the art and that is pharmaceutically acceptable may be used, polycationic biopolymers are presently preferred. A presently preferred polycationic biopolymer is chitosan.

With regard to any of the above therapeutic agent delivery means involving a shell-type structure or a particle into which a therapeutic agent is imbedded, the therapeutic effect can be enhanced by including a targeting moiety into the carrier system. Such targeting moieties and techniques are well-known in the art. For example, without limitation, the surface of a carrier could be modified with antibodies to surface receptors known to be associated with the disease being treated. Interaction between the antibody and the receptor would result in the carrier being bound to the surface at the target site permitting release of the therapeutic agent over virtually any desired time period.

Of course, small molecule modification of the carrier surface would also be effective. For example, without limitation, NHS (N-hydroxysuccinimidyl) esters would be amenable to transesterification with hydroxyl-substituted molecules in the target tissue or to amide formation by reaction of protein amine groups in the tissue.

Another targeting approach would be to modify the target site itself. For example, again without limitation, NHS-biotin might be conjugated to amine groups in proteins known to populate the diseased tissue. This would render the tissue in that region particularly adhesive with regard to carriers, the surface of which has been modified with avidin.

Additional targeting techniques and combinations will be apparent to those skilled in the art based on the disclosure herein; all such techniques and combination are within the scope of this invention.

What is claimed:

1. A method of treating a vascular disease, comprising:
   providing a device having a regional delivery interface comprising a therapeutic agent;
   contacting the regional delivery interface with a surface of a segment of a vessel that includes a region that is afflicted with a vascular disease, wherein:
      the regional delivery interface is at least about 40 mm in length, and the regional delivery interface contacts the vessel segment surface not only at the afflicted region but also at a non-afflicted region at the periphery of the afflicted region; and
   delivering the therapeutic agent onto or into the vessel segment surface from the regional delivery interface in contact with the vessel segment surface,
      wherein the therapeutic agent is delivered simultaneously to both the afflicted region and the non-afflicted region in a therapeutically effective amount and in a substantially uniform dose,
      wherein the therapeutic agent is provided in a pharmaceutically acceptable composition, and
      wherein the pharmaceutically acceptable composition comprises a micelle, a worm micelle, or a polymerosome.

2. The method of claim 1, wherein the entire length of the regional delivery interface contacts the vessel segment surface.

3. The method of claim 1, wherein two or more segments of the regional delivery interface contact the vessel segment surface provided that one or more of the regional delivery interface segments contact(s) the vessel segment surface at afflicted regions and one or more regional delivery interface segments contact(s) the vessel segment at non-afflicted regions of the vessel segment.

4. The method of claim 1, wherein the device comprises a balloon.

5. The method of claim 4, wherein the balloon comprises two or more first diameters that define portions of an outer surface of the balloon that are in contact with the vessel segment surface and one or more second diameters that define portions of an outer surface that are not in contact with the vessel segment surface, wherein:

two of the portions of the balloon that are in contact with the vessel segment surface contact the vessel segment surface in non-afflicted regions at the periphery of the afflicted region.

6. The method of claim 4, wherein the regional delivery interface comprises a coating on the outer surface of the balloon, the coating comprising the therapeutic agent.

7. The method of claim 4, wherein the balloon is microporous and the therapeutic agent is contained in a fluid for inflating the balloon.

8. The method of claim 4, wherein the regional delivery interface comprises a plurality of micro-needles disposed at an outer surface of the balloon.

9. The method of claim 1, wherein the device comprises an implantable medical device and the vessel segment surface is a luminal surface.

10. The method of claim 9, wherein the implantable medical device is a stent.

11. The method of claim 1, wherein the vascular disease is selected from the group consisting of atherosclerosis, restenosis, vulnerable plaque and peripheral arterial disease.

12. The method of claim 1, wherein the therapeutic agent induces apoptosis of macrophages and/or of foam cells.

13. The method of claim 12, wherein the therapeutic agent comprises a bisphosphonate.

14. The method of claim 13, wherein the bisphosphonate is selected from the group consisting of etidronate, clodronate, tiludronate, pamidronate, dimethyl pamidronate, alendronate, ibandronate, risedronate and zeledronate.

15. The method of claim 13, wherein the pharmaceutically acceptable composition comprises a coacervate of the bisphosphonate.

16. The method of claim 15, wherein the coacervate is a polycationic biopolymer.

17. The method of claim 16, wherein the polycationic biopolymer is chitosan.

18. The method of claim 1, wherein the regional delivery interface is between about 40 mm and about 200 mm in length.

19. The method of claim 1, wherein the regional delivery interface is between about 40 mm and about 100 mm in length.

20. The method of claim 1, wherein the regional delivery interface is at least about 1-2 mm longer than the length between a first afflicted region and a second afflicted region, wherein the first afflicted region and second afflicted region are afflicted regions that are furthest apart among all afflicted regions of the vessel segment surface, and wherein the regional delivery interface fully encompasses the first and second afflicted regions.

21. The method of claim 1, wherein the regional delivery interface is at least about 5-10 mm longer than the length between a first afflicted region and a second afflicted region, wherein the first afflicted region and second afflicted region are afflicted regions that are furthest apart among all afflicted regions of the vessel segment surface, and wherein the regional delivery interface fully encompasses the first and second afflicted regions.

22. A method of treating a vascular disease, comprising:

providing a device having a regional delivery interface comprising a bisphosphonate;

contacting the regional delivery interface with a surface of a segment of a vessel that includes a region that is afflicted with a vascular disease, wherein:

the regional delivery interface contacts the vessel segment surface not only at the afflicted region but also at a non-afflicted region at the periphery of the afflicted region; and delivering the bisphosphonate onto or into the vessel segment surface from the regional delivery interface in contact with the vessel segment surface, wherein the bisphosphonate is delivered simultaneously to both the afflicted region and the non-afflicted region in a therapeutically effective amount and in a substantially uniform dose, wherein the bisphosphonate is provided in a pharmaceutically acceptable composition, and wherein the pharmaceutically acceptable composition comprises a micelle, a worm micelle, or a polymerosome.

23. The method of claim 22, wherein the bisphosphonate is selected from the group consisting of etidronate, clodronate, tiludronate, pamidronate, dimethyl pamidronate, alendronate, ibandronate, risedronate and zeledronate.

24. The method of claim 22, wherein the vascular disease is selected from the group consisting of atherosclerosis, restenosis, vulnerable plaque and peripheral arterial disease.

* * * * *